(12) United States Patent
Volz et al.

(10) Patent No.: US 8,680,316 B2
(45) Date of Patent: Mar. 25, 2014

(54) PROCESS FOR THE PREPARATION OF CIS-1-AMMONIUM-4-ALKOXYCYCLOHEXANE-CARBONITRILE SALTS

(75) Inventors: Frank Volz, Köln (DE); Albert Schnatterer, Leverkusen (DE); Bernardus Kaptein, Sittard (NL); Anna Maria Cornelia Francisca Castelijns, Spaubeek (NL)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/330,307

(22) Filed: Dec. 19, 2011

(65) Prior Publication Data

US 2012/0197035 A1    Aug. 2, 2012

Related U.S. Application Data

(60) Provisional application No. 61/427,913, filed on Dec. 29, 2010.

(30) Foreign Application Priority Data

Dec. 22, 2010 (EP) .................................. 10196473

(51) Int. Cl.
  *C07C 255/46* (2006.01)
(52) U.S. Cl.
  USPC ........................................................ 558/431
(58) Field of Classification Search
  USPC ........................................................ 558/431
  See application file for complete search history.

(56) References Cited

U.S. PATENT DOCUMENTS

| | | | |
|---|---|---|---|
| 5,082,970 A * | 1/1992 | Braish | 564/424 |
| 5,462,913 A | 10/1995 | Fischer et al. | |
| 5,508,436 A | 4/1996 | Fischer et al. | |
| 5,622,917 A | 4/1997 | Fischer et al. | |
| 5,830,826 A | 11/1998 | Fischer et al. | |
| 5,994,274 A | 11/1999 | Fischer et al. | |
| 6,114,374 A | 9/2000 | Lieb et al. | |
| 6,140,358 A | 10/2000 | Lieb et al. | |
| 6,316,486 B1 | 11/2001 | Lieb et al. | |
| 6,358,887 B1 | 3/2002 | Fischer et al. | |
| 6,451,843 B1 | 9/2002 | Lieb et al. | |
| 6,458,965 B1 | 10/2002 | Lieb et al. | |
| 6,472,419 B1 | 10/2002 | Fischer et al. | |
| 6,861,391 B1 | 3/2005 | Fischer et al. | |
| 2003/0171219 A1 | 9/2003 | Lieb et al. | |
| 2003/0216260 A1 | 11/2003 | Ruther et al. | |
| 2005/0187220 A1 | 8/2005 | Sundermann et al. | |
| 2008/0081807 A1 | 4/2008 | Lieb et al. | |

FOREIGN PATENT DOCUMENTS

WO    WO 2008/128058 A1  *  10/2008

OTHER PUBLICATIONS

Introduction to Organic Laboratory Techniques, Pavia (1990) (Technique 5 on pp. 577-596).*
Introduction to Organic Laboratory Techniques, Pavia (1990) (Technique 7 on pp. 617-637).*
Edward, J.T. and Jitrangsri, C., "Stereochemistry of the Bucherer-Bergs and Strecker Reactions of 4-*tert*-Butylcyclohexanone," *Can. J. Chem.* 53:3339-3350, Canadian Science Publishing, Canada (1975).
Maki, Y. and Masugi, T., "Studies of Alicyclic α-Amino Acids. II. Synthesis and Unequivocal Assignment of Stereochemistry of 1-Amino-*trans*- and *cis*-4-hydroxycyclohexane-1-carboxylic Acids," *Chem. Pharm. Bull.* 21(4):685-691, The Pharmaceutical Society of Japan, Japan (1973).
Munday, L., "Amino Acids of the Cyclohexane Series. Part I," *J. Chem. Soc.* 4372-4379, American Chemical Society, United States (1961).
Munday, L., "Alkylcyclohexanones in the Strecker and Bucherer Hydantoin Syntheses," *Nature* 190(4781):1103-1104, Nature Publishing Group, England (1961).

* cited by examiner

*Primary Examiner* — Shawquia Young
(74) *Attorney, Agent, or Firm* — Sterne, Kessler, Goldstein & Fox P.L.L.C.

(57) ABSTRACT

The present invention relates to a novel process for the preparation of cis-1-ammonium-4-alkoxycyclohexanecarbonitrile salts and to novel intermediates or starting compounds which are passed through or used in the process according to the invention.

14 Claims, No Drawings

PROCESS FOR THE PREPARATION OF CIS-1-AMMONIUM-4-ALKOXYCYCLOHEXANE-CARBONITRILE SALTS

The present invention relates to a novel process for the preparation of cis-1-ammonium-4-alkoxycyclohexanecarbonitrile salts and to novel intermediates or starting compounds which are passed through or used in the process according to the invention. cis-1-Ammonium-4-alkoxycyclohexanecarbonitrile salts are important intermediates in the synthesis of insecticidal active substances.

Substituted cyclic ammonium salts are accessible by reaction of the corresponding aminonitriles with acids. In this connection, compounds of the formula (I)

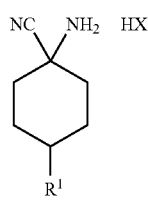

(I)

are obtained as a mixture of isomers of the formulae (cis-I) and (trans-I)

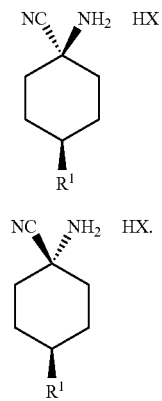

(cis-I)

(trans-I)

Salts of corresponding 4-substituted 1-aminocyclohexanecarbonitriles are described in the literature (L. Munday, J. Chem. Soc., 1961, 4372-4379; L. Munday, Nature, 1961, 190, 1103-1104; Y. Maki and T. Masugi, Chem. Pharm. Bull., 1973, 21, 685-691; J. T. Edward and C. Jitrangsri, Can. J. Chem., 1975, 53, 3339-3350). The salts described here are exclusively hydrochlorides of the corresponding 1-aminocyclohexanecarbonitriles. They are isolated either with an unfavourable cis/trans-isomer ratio up to the pure trans-compound. This is not surprising since a corresponding stereochemistry is described in the abovementioned literature for Strecker reaction products (aminonitriles) and subsequently the salts thereof. Since the cis-isomer is desired for the process described here, the processes known in the literature are not suitable.

The compounds of the formulae (cis-I) and (trans-I) can be prepared according to the process described in EP-A-0595130 and WO 2003/080557; the compounds of the formulae (cis-I) and (trans-I) are novel.

The synthesis of the cis/trans-isomer mixture as corresponding hydrochloride has already been described as intermediate compound in WO 2008/128058. However, a separation of the two isomers was not carried out and accordingly the selective preparation of the cis-compound is not described.

The object of the present invention is to make available a novel economic process for the selective preparation of cis-1-ammonium-4-alkoxycyclohexanecarbonitrile salts starting from cis/trans-amino-4-alkoxycyclohexanecarbonitriles.

A subject-matter of the present invention is a process for the preparation of compounds of the formulae (cis-I) and (trans-I)

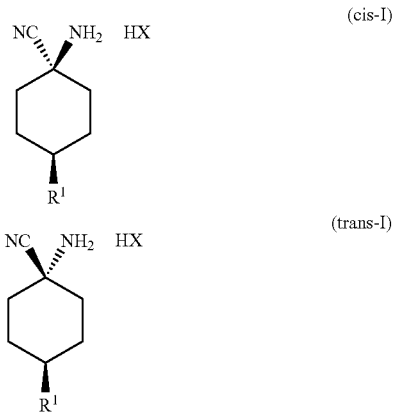

(cis-I)

(trans-I)

in which
R$^1$ is OR$^2$,
R$^2$ is alkyl,
HX is HCl, H$_2$SO$_4$, H$_3$PO$_4$, HCOOH, HO$_2$CCO$_2$H, p-toluenesulphonic acid or methanesulphonic acid.

The Strecker reaction is generally carried out in such a way that a substituted cyclic ketone of the formula (II)

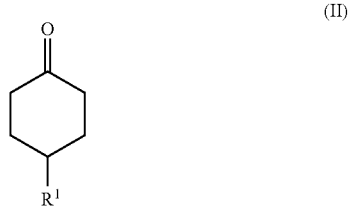

(II)

in which R$^1$ has the meanings given above is reacted with alkali metal cyanide, ammonium chloride and ammonia (or directly with hydrocyanic acid and ammonia) in mixtures of organic solvents and water in a two-phase system, and the aminonitrile of the formula (III)

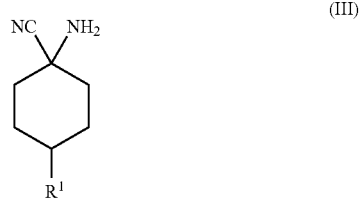

(III)

in which R$^1$ has the meanings given above
thereby produced is isolated.

In this connection, the aminonitriles of the formula (III) are usually obtained as mixtures of cis-isomer (cis-III):

(cis-III)

and trans-isomer (trans-III):

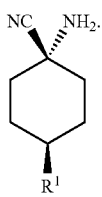

(trans-III)

These substituted cyclic aminonitriles of the formula (III) can be converted, by reaction with acids (HX) in organic solvents, to mixtures of the corresponding ammonium salts of the formula (I)

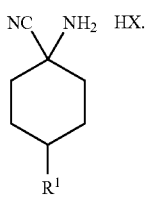

(I)

In this connection, the compounds of the formula (I) are obtained as mixtures of cis-isomer (cis-I) and trans-isomer (trans-I).

Novel compounds of the formulae (cis-I) and (trans-I)

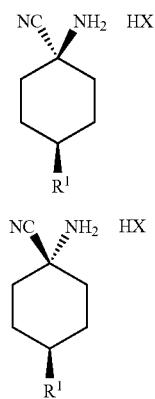

have been found in which
$R^1$ and HX have the meanings given above.

Preference is given to compounds of the formulae (cis-I) and (trans-I) in which
$R^1$ is $OR^2$,
$R^2$ is alkyl,
HX is $H_2SO_4$, $H_3PO_4$, HCOOH, $HO_2CCO_2H$, p-toluenesulphonic acid or methanesulphonic acid.

Particular preference is given to compounds of the formulae (cis-I) and (trans-I) in which
$R^1$ is $OR^2$,
$R^2$ is $C_1$-$C_6$-alkyl,
HX is $H_2SO_4$, $H_3PO_4$, HCOOH or $HO_2CCO_2H$.

Very particular preference is given to compounds of the formulae (cis-I) and (trans-I) in which
$R^1$ is $OR^2$,
$R^2$ is methyl, ethyl or n-propyl, (emphasis is placed on methyl),
HX is HCOOH.

Substituted cyclic ammonium nitrile salts of the general formula (I) are required as intermediates for many compounds (for example from EP-A-596 298, WO 95/26954, WO 95/20572, EP-A 668 267, WO 96/25395, WO 96/35664, WO 97/01535, WO 97/02243, WO 97/36868, WO 98/05638, WO 99/43649, WO 99/48869, WO 99/55673, WO 01/23354 and WO 01/74770).

In this connection, it may be advantageous for certain of these compounds, for example which have become known from EP-A-596 298, WO 95/26954, WO 95/20572, EP-A 668 267, WO 96/25395, WO 96/35664, WO 97/01535, WO 97/02243, WO 97/36868, WO 98/05638, WO 99/43649, WO 99/48869, WO 99/55673, WO 01/23354 and WO 01/74770, to use the corresponding cis-configured ammonium nitrile salt of the formula (cis-I).

Surprisingly, according to the process according to the invention, the cis/trans-isomer mixture of aminonitriles (cis-III and trans-III) can be separated, via their corresponding ammonium salts of the formulae (cis-I) and (trans-I), because of differing solubility in organic solvents.

Use may preferably be made, as alkali metal cyanides for the synthesis of the cis/trans-isomer mixture of the formula (III), of lithium cyanide, sodium cyanide or potassium cyanide; particular preference is given to sodium cyanide or potassium cyanide; very particular preference is given to sodium cyanide.

The amount of alkali metal cyanide, based on the ketone of the formula (II), lies between 0.8 and 3 mol. Use is preferably made of amounts between 1 and 2.5 mol, based on the ketone of the formula (II); particular preference is given to amounts between 1 and 1.5 mol per mole of ketone (II).

The amount of ammonium chloride is between 0.9 and 3.5 mol per mole of ketone (II). Preference is given to amounts between 1 and 3 mol per mole of ketone (II); particular preference is given to amounts between 1.1 and 2 mol per mole of ketone (II).

The amount of ammonia, based on the ketone of the formula (II), lies between 1 and 8 mol. Use is preferably made of amounts between 1 and 5 mol, based on the ketone of the formula (II); particular preference is given to amounts between 1 and 3 mol per mole of ketone (II).

The reaction temperature of the process according to the invention lies between 20 and 100° C.; preference is given to a temperature range from 20 to 70° C.

Suitable solvents are preferably water, and also alcohol (e.g., methanol, ethanol, propanol, butanol)/water mixtures, and also two-phase systems consisting of water and organic solvents, such as methyl tert-butyl ether, toluene, xylene, dichloromethane, chloroform, carbon tetrachloride, alkyl acetates (alkyl=e.g., methyl, ethyl, propyl or isopropyl) or tetrahydrofuran. Solvents which are particularly preferred are water, water/alcohol mixtures and following two-phase systems consisting of water and organic solvents, such as MTBE, toluene, xylene, ethyl acetate or tetrahydrofuran.

The isolation of the mixture of isomers of cis/trans-aminonitrile of the formula (III) is carried out by liquid/liquid extraction. The aminonitriles of the formula (III) obtained can be extracted with organic solvents, such as toluene, dichloromethane, trichloromethane, carbon tetrachloride, alkyl acetates (alkyl=e.g., methyl, ethyl, propyl or isopropyl), methyl tert-butyl ether, diethyl ether, diisopropyl ether, tetrahydrofuran, aliphatic and aromatic hydrocarbons, such as n-hexane, benzene, toluene and xylene, which may be substituted by fluorine and chlorine atoms, such as methylene chloride, dichloromethane, trichloromethane, carbon tetrachloride, fluorobenzene, chlorobenzene or dichlorobenzene, or ethers, such as diethyl ether, diisopropyl ether, diphenyl ether, methyl tert-butyl ether, isopropyl ethyl ether, dioxane, dimethyl glycol or tetrahydrofuran.

Acid is added to the solution obtained of the mixture of isomers of cis/trans-aminonitriles (III) in one of the abovementioned organic solvents, preferably in methyl tert-butyl ether, toluene, dichloromethane, chloroform, carbon tetrachloride, alkyl acetates (alkyl=e.g., methyl, ethyl, propyl or isopropyl) or tetrahydrofuran and particularly preferably in methyl tert-butyl ether, toluene, ethyl acetate, methyl acetate or tetrahydrofuran. Preference is given to hydrochloric acid, sulphuric acid, phosphoric acid, formic acid, oxalic acid, p-toluenesulphonic acid or methanesulphonic acid, particular preference is given to sulphuric acid, phosphoric acid, formic acid, oxalic acid, p-toluenesulphonic acid or methanesulphonic acid, very particular preference is given to formic acid, sulphuric acid, oxalic acid or phosphoric acid and emphasis is placed on formic acid. The isolation of the solids of the formula (I) obtained is carried out by filtration of the reaction mixture and drying of the filter cake.

The process according to the invention can, for example, be illustrated by the following scheme:

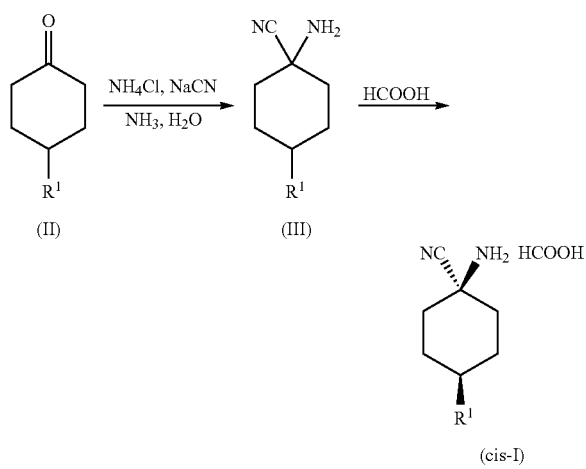

A subject-matter of this invention is likewise a process for the isomerisation of the undesirable trans-isomer of the formula (trans-III),

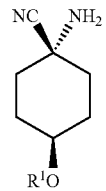

in which
R$^1$ has the abovementioned meanings
or the ammonium salt of the formula (trans-I),

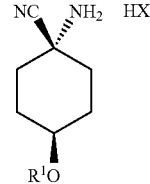

in which
R$^1$, R$^2$ and HX have the meanings given above
to give a cis/trans-isomer mixture of the formula (III), as is obtained in the Strecker reaction.

The process according to the invention can, for example, be illustrated by the following scheme:

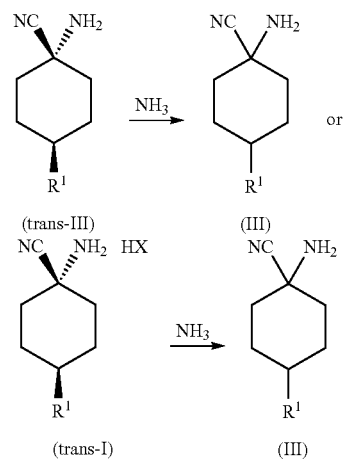

The amount of ammonia, based on the ketone of the formula (II), lies between 1 and 5 mol. Use is preferably made of amounts between 1 and 3 mol, based on the ketone of the formula (III); particular preference is given to amounts between 1 and 2 mol per mole of ketone (III).

Use is made, as solvent, of a mixture of water/ammonia or correspondingly the solvents described above.

The reaction temperature of the process according to the invention lies between 20 and 100° C.; preference is given to a temperature range from 20 to 60° C., particularly preferably of 50-60° C.

Surprisingly, according to the process according to the invention, the isomerisation of the undesirable trans-isomers (trans-I and trans-III) can be carried out under the conditions of the Strecker reaction, which is advantageous from a technical viewpoint. In addition, it is possible to carry out the Strecker reaction in a 2-phase mixture of organic solvents and water, which is very efficient from a technical viewpoint. Such examples of this procedure are not described in the literature.

The process according to the invention can, for example, be clarified by the following scheme:

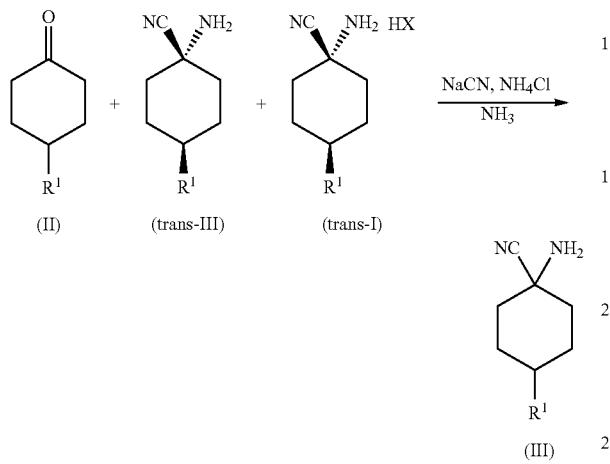

The reaction is carried out analogously to the Strecker reaction. For complete isomerisation of the admixed trans-isomers (trans-III and trans-I), the amount of ammonia has to be increased by 2-5 mol per mole of trans-isomers (trans-III and trans-I), preferably 2-3 mol and particularly preferably 1.5-2 mol.

The reaction temperature of the process according to the invention lies between 20 and 80° C.; preference is given to a temperature range of 30-70° C.

PREPARATION EXAMPLES

Example 1 cis/trans-1-Amino-4-methoxycyclohexanecarbonitrile

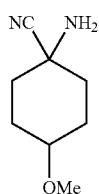

NaCN (79.6 g, 1 eq., 1.56 mol, 96%, as saturated solution in $H_2O$) and ammonia (265.3 g, 2.5 eq., 3.9 mol, 25% in $H_2O$) are added dropwise with vigorous stirring (precision-bearing stirrer) in 1.5 hours to a solution of 4-methoxycyclohexanone (204.4 g, 97.9% (by GC), 1.56 mol, freshly distilled: 59.9° C./3 mbar), $NH_4Cl$ (92.3 g, 1.1 eq., 1.72 mol, 99.5%, as saturated solution in $H_2O$ (250 g)) and toluene (475 g, 30% by weight of the total reaction charge). After a subsequent stirring time of 1 hour, the phases are separated and the aqueous phase is extracted with toluene. The toluene phase is distilled under reduced pressure to a total amount of 700 g (if all the toluene is removed, then 246.2 g of oil remain with a content (GC area %) of on average 85%). From this result: 209.3 g of cis/trans-1-amino-4-methoxycyclohexanecarbonitrile (1.36 mol, 87%, cis: trans=55:45, GC-MS: $[M]^+$: m/z=154, $[M-H]^+$: m/z=153).

$^1$H NMR (600 MHz, $(CD_3)_2SO$): δ=9.63 (br. s, 2H, $NH_2$), 3.46 (m, 1H, CHOMe, cis), 3.25 (s, 3H, Me, trans), 3.22 (s, 3H, Me, cis), 3.$\overline{15}$ (m, 1H, CHOMe, trans), 1.29-2.27 (m, 8H, $CH_2$). $^{13}$C NMR (150 MHz, $(CD_3)_2SO$): δ=117.94 (CN, cis+trans), 75.7 (CHOMe, trans), 71.2 (CHOMe, cis), 55.6 ($H_3CO$, trans), 5$\overline{5.4}$ ($H_3CO$, cis), 51.5 ($\overline{C}NH_2$, cis), 51.3 ($CNH_2$, trans), 31.4 ($H_2NC\overline{C}H_2$, trans), 28.$\overline{1}$ ($H_2NCCH_2$, cis$\overline{)}$, 27.6 (MeOCH$\overline{CH_2}$, trans), 25.6 (MeOCH$\overline{CH_2}$, cis). GC-MS: $[M]^+$: m/z=154.

Example 2

Synthesis of cis-1-amino-4-methoxycyclohexanecarbonitrile hydrogen formate

An amount of MTBE of 1.4 kg is added to the toluene solution of cis/trans-1-amino-4-methoxycyclohexanecarbonitrile obtained in Example 1. An amount of cis-1-amino-4-methoxycyclohexanecarbonitrile hydrogen formate seed crystals of 1 mol % (2.73 g, 13.6 mmol) is added with stirring at ambient temperature. Formic acid (32.3 g, 26.5 ml, 0.7 mol) is then added dropwise over 15 minutes and the solution obtained is cooled with an ice bath for 2 hours. The precipitated ammonium formate is filtered off and the filter cake is washed with toluene and MTBE. After drying, cis-1-amino-4-methoxycyclohexanecarbonitrile hydrogen formate (118.7 g, content: GC area % after derivatizing with trifluoroacetic anhydride: 82.8%, cis/trans=95:5, from which result: 98.3 g, 0.49 mol, 32% (based on 4-methoxycyclohexanone), LC-MS: $[M-O_2CH]^+$: m/z=155.1) is obtained as colourless solid.

Example 3

Isomerisation and Strecker Reaction

The mother liquor is prepared as follows for the recycling: first MTBE is removed under reduced pressure as thoroughly as possible and the toluene solution is transferred into a 2-litre three-necked flask. 4-Methoxycyclohexanone (62.8 g, 97.9%, 0.49 mol) isolated cis-1-amino-4-methoxycyclohexanecarbonitrile hydrogen formate from Example 2), $NH_4Cl$ (29.0 g, 1.1 eq., 0.49 mol, 99.5%, as saturated solution in $H_2O$) and toluene (475 g) are then added. NaCN (25.0 g, 1 eq., 0.49 mol, 96%, as saturated solution in $H_2O$) and ammonia (83.3 g, 2.5 eq., 1.22 mol, 25% in $H_2O$, additionally for the isomerisation of the recycled aminonitrile: $NH_3$ (47.9 g, 0.702 mol, 25% in $H_2O$)) are metered in separately with vigorous stirring over 1.5 hours. After 1 hour at 60° C., the phases are separated and the aqueous phase is extracted with toluene. After removal of the toluene under reduced pressure, 242.3 g of oil with a content (GC area %) of on average 85% are obtained. From this result: 206.0 g of cis/trans-1-amino-4-methoxycyclohexanecarbonitrile (1.34 mol, 85%, cis: trans=55:45, GC-MS: $[M]^+$: m/z=154, $[M-H]^+$: m/z=153).

The invention claimed is:

1. A compound of formulae (cis-I) or (trans-I)

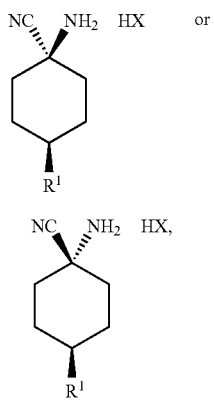

in which
  $R^1$ is $OR^2$,
  $R^2$ is alkyl, and
  HX is $H_2SO_4$, $H_3PO_4$, HCOOH, $HO_2CCO_2H$, p-toluenesulphonic acid or methanesulphonic acid.

2. The compound of formulae (cis-I) or (trans-I) according to claim 1, in which
  $R^1$ is $OR^2$,
  $R^2$ is $C_1$-$C_6$-alkyl, and
  HX is $H_2SO_4$, $H_3PO_4$, HCOOH or $HO_2CCO_2H$.

3. The compound of formulae (cis-I) (trans-I) according to claim 1, in which
  $R^1$ is $OR^2$,
  $R^2$ is methyl, ethyl or n-propyl, and
  HX is HCOOH.

4. A compound of formula (cis-I) according to claim 1, in which $R^1$ and HX are as defined in claim 1.

5. A process for preparing the compound of formulae (cis-I) or (trans-I) according to claim 1,
  comprising reacting a compound of formula (II)

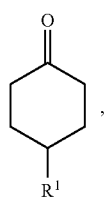

in which
  $R^1$ is as defined in claim 1,
  with an alkali metal cyanide, ammonium chloride and ammonia in mixtures of organic solvents and water in a two-phase system, wherein the amount of ammonia is between 1 and 8 mol per mol of the compound of formula (II), and at a reaction temperature between 20 and 100° C.,
  to give a compound of formula (III)

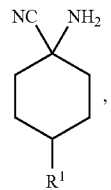

in which
  $R^1$ has the abovementioned meanings,
  mixing the compound of formula (III) with HX, HX is as defined in claim 1, and
  separating the compound of formulae (cis-I) or (trans-I) by filtration.

6. A process for selectively preparing the compound of formula (cis-I)

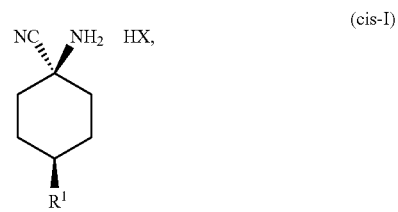

in which
  $R^1$ is $OR^2$,
  $R^2$ is alkyl, and
  HX is, $H_2SO_4$, $H_3PO_4$, HCOOH, $HO_2CCO_2H$, p-toluenesulphonic acid or methanesulphonic acid,
  comprising reacting a compound of formula (III):

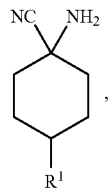

in which
  $R^1$ has, the abovementioned meanings,
  with HX, HX having the meanings given above,
  seeding the compound (cis-I),
  and separating the compound (cis-I) by filtration.

7. A process for preparing a compound of formula (III)

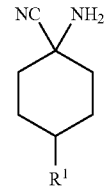

in which
  $R^1$ is $OR^2$, and
  $R^2$ is alkyl, comprising reacting compounds of formulae (trans-III) and (trans-I):

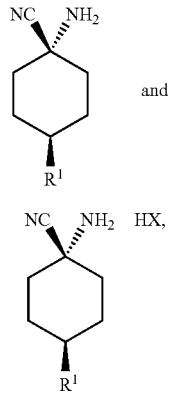

in which
R¹ is as defined above,
and
HX is $H_2SO_4$, $H_3PO_4$, HCOOH, $HO_2CCO_2H$, p-toluene-sulphonic acid or methanesulphonic acid,
with aqueous ammonia, or with ammonia in mixtures of organic solvents and water.

8. A process for preparing a compound of formula (III),

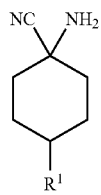

in which
R¹ is $OR^2$, and
R² is alkyl,
comprising mixing compounds of formulae (trans-III) and (trans-I)

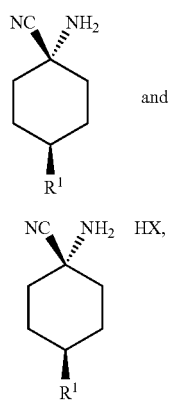

in which
R¹ is as defined above, and
HX is $H_2SO_4$, $H_3PO_4$, HCOOH, $HO_2CCO_2H$, p-toluene-sulphonic acid or methanesulphonic acid, with a compound of formula (II)

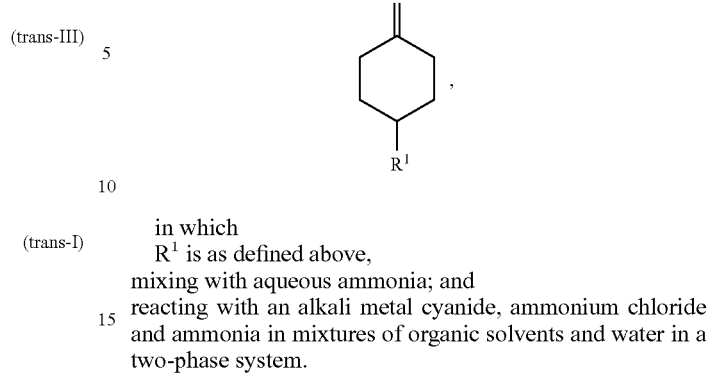

in which
R¹ is as defined above,
mixing with aqueous ammonia; and
reacting with an alkali metal cyanide, ammonium chloride and ammonia in mixtures of organic solvents and water in a two-phase system.

9. A process for selectively preparing a compound of formula (cis-I),

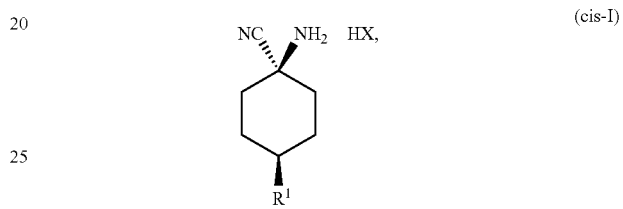

in which
R¹ is $OR^2$,
R² is alkyl, and
HX is, $H_2SO_4$, $H_3PO_4$, HCOOH, $HO_2CCO_2H$, p-toluene-sulphonic acid or methanesulphonic acid,
comprising reacting a compound of formula (II)

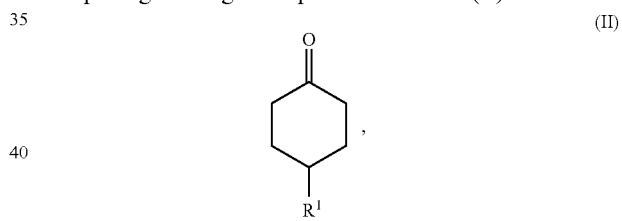

in which
R¹ is as defined above,
with an alkali metal cyanide, ammonium chloride and ammonia in mixtures of organic solvents and water in a two-phase system, wherein the amount of ammonia is between 1 and 8 mol per mol of the compound of formula (II), and at a reaction temperature between 20 and 100° C.,
to give a compound of formula (III)

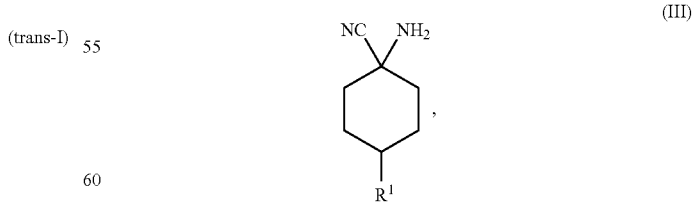

in which
R¹ R is as defined above;
mixing the compound of formula (III) with HX, HX is as defined above; and
separating the compound of formula (cis-I) by filtration.

10. A mixture of compounds of formulae (cis-I) and (trans-I):

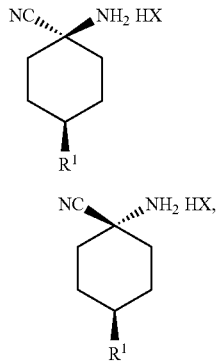

(cis-I)

and (trans-I)

in which
R¹ is OR²,
R² is alkyl, and
HX is, $H_2SO_4$, $H_3PO_4$, HCOOH, $HO_2CCO_2H$, p-toluenesulphonic acid or methanesulphonic acid,
which is obtained by a process comprising reacting a compound of formula (II)

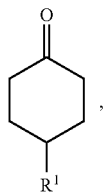

(II)

in which
R¹ is as defined above,
with an alkali metal cyanide, ammonium chloride and ammonia in mixtures of organic solvents and water in a two-phase system, wherein the amount of ammonia is between 1 and 8 mol per mol of the compound of formula (II), and at a reaction temperature between 20 and 100° C., to give a compound of formula (III)

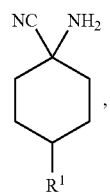

(III)

in which
R¹ is as defined above;
mixing the compound of formula (III) with HX, HX is as defined above; and
separating the compound of formula (cis-I) by filtration.

11. The mixture of compounds according to claim 10, which is obtained by a process comprising reacting a compound of formula (III):

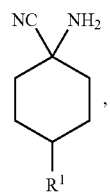

(III)

in which
R¹ is as defined in claim 10, with HX, HX is as defined in claim 10;
seeding the compound of formula (cis-I);
and
separating the compound of formula (cis-I) by filtration.

12. The process according to claim 5, wherein the amount of ammonia is between 2 and 5 mol per mol of the compound of formula (II) according to claim 5.

13. The process according to claim 9, wherein the amount of ammonia is between 2 and 5 mol per mol of the compound of formula (II) according to claim 9.

14. The mixture according to claim 11, which is obtained by the process according to claim 11, wherein the amount of ammonia is between 2 and 5 mol per mol of the compound of formula (II) according to claim 11.

* * * * *